(12) United States Patent
Govrin (10) Patent No.: US 11,395,406 B2
(45) Date of Patent: *Jul. 19, 2022

(54) CAMERA HEAD

(71) Applicant: SCOUTCAM Ltd., Omer (IL)

(72) Inventor: Amir Govrin, Ramat Gan (IL)

(73) Assignee: SCOUTCAM LTD., Omer (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/107,127

(22) Filed: Nov. 30, 2020

(65) Prior Publication Data

US 2021/0084766 A1 Mar. 18, 2021

Related U.S. Application Data

(63) Continuation-in-part of application No. 16/534,559, filed on Aug. 7, 2019, now Pat. No. 10,887,992, (Continued)

(30) Foreign Application Priority Data

Jun. 11, 2015 (IL) .......................................... 239386

(51) Int. Cl.
| | |
|---|---|
| H05K 1/14 | (2006.01) |
| A61B 1/05 | (2006.01) |
| A61B 1/06 | (2006.01) |
| G02B 23/24 | (2006.01) |
| H04N 5/225 | (2006.01) |

(52) U.S. Cl.
CPC ............ *H05K 1/144* (2013.01); *A61B 1/051* (2013.01); *A61B 1/0607* (2013.01); *A61B 1/0676* (2013.01); *A61B 1/0684* (2013.01); *G02B 23/243* (2013.01); *G02B 23/2469* (2013.01); *G02B 23/2484* (2013.01); *H04N 5/2257* (2013.01); *H05K 2201/042* (2013.01); *H05K 2201/09027* (2013.01); *H05K 2201/10106* (2013.01); *H05K 2201/10121* (2013.01); *H05K 2201/10151* (2013.01); *H05K 2201/10303* (2013.01); *H05K 2201/10318* (2013.01); *H05K 2201/2036* (2013.01)

(58) Field of Classification Search
USPC .......................................................... 348/68
See application file for complete search history.

(56) References Cited

U.S. PATENT DOCUMENTS

| | | |
|---|---|---|
| 4,491,865 A | 1/1985 | Danna et al. |
| 4,607,622 A | 8/1986 | Fritch et al. |
| (Continued) | | |

FOREIGN PATENT DOCUMENTS

| | | |
|---|---|---|
| CN | 2885155 Y | 4/2007 |
| CN | 103976763 A | 8/2014 |
| (Continued) | | |

*Primary Examiner* — Behrooz M Senfi
(74) *Attorney, Agent, or Firm* — The Roy Gross Law Firm, LLC; Roy Gross (57) ABSTRACT

Disclosed is a video camera head comprised of at least two rigid printed circuit boards (PCBs) arranged in parallel planes. The at least two PCBs are mechanically supported one above the other by at least two external pins attached to the perimeters of the PCBs. The external pins fit into grooves cut into the edges of the PCBs. Several embodiments of the video camera head are described.

19 Claims, 8 Drawing Sheets

Related U.S. Application Data which is a continuation of application No. 15/579,410, filed as application No. PCT/IL2016/050603 on Jun. 9, 2016, now Pat. No. 10,420,216.

(56) References Cited

U.S. PATENT DOCUMENTS

| | | | |
|---|---|---|---|
| 5,309,324 A | 5/1994 | Herandez et al. | |
| 5,323,766 A | 6/1994 | Uram | |
| 5,797,849 A | 8/1998 | Vesely et al. | |
| 6,398,721 B1 | 6/2002 | Nakamura et al. | |
| 6,817,870 B1 | 11/2004 | Kwong et al. | |
| 7,474,390 B2 | 1/2009 | Robinson et al. | |
| 8,622,896 B1 | 1/2014 | Termanini | |
| 9,750,638 B2 | 9/2017 | Bourne et al. | |
| 10,420,216 B2 * | 9/2019 | Govrin | A61B 1/0684 |
| 10,426,324 B2 | 10/2019 | Nakamura et al. | |
| 10,887,992 B2 * | 1/2021 | Govrin | A61B 1/051 |
| 2003/0088260 A1 | 5/2003 | Smealley et al. | |
| 2004/0171914 A1 | 9/2004 | Avni | |
| 2007/0129605 A1 | 6/2007 | Schaaf | |
| 2008/0167527 A1 | 7/2008 | Slenker et al. | |
| 2008/0214891 A1 | 9/2008 | Slenker et al. | |
| 2010/0185052 A1 * | 7/2010 | Chang | A61B 1/051 |
| | | | 600/112 |
| 2010/0305503 A1 | 12/2010 | Fang et al. | |
| 2011/0112405 A1 | 5/2011 | Barthe et al. | |
| 2012/0206583 A1 | 8/2012 | Hoshi et al. | |
| 2012/0265010 A1 | 10/2012 | Uram | |
| 2013/0050954 A1 * | 2/2013 | Albrecht, III | H05K 7/20454 |
| | | | 361/720 |
| 2013/0155396 A1 | 6/2013 | Deliwala | |
| 2013/0205936 A1 | 8/2013 | Schmieding et al. | |
| 2013/0303003 A1 | 11/2013 | Tsang et al. | |
| 2014/0296628 A1 * | 10/2014 | Kirma | A61B 1/00039 |
| | | | 600/103 |
| 2015/0025539 A1 | 1/2015 | Alvarez et al. | |
| 2015/0045820 A1 | 2/2015 | Kahook | |
| 2015/0141755 A1 | 5/2015 | Tesar | |
| 2015/0342690 A1 * | 12/2015 | Zubiate | A61B 1/051 |
| | | | 606/130 |
| 2017/0095142 A1 | 4/2017 | McDowall | |
| 2018/0078410 A1 | 3/2018 | Gavanescu | |
| 2018/0110404 A1 | 4/2018 | Devaiah et al. | |
| 2018/0125707 A1 | 5/2018 | Khader et al. | |
| 2021/0085162 A1 * | 3/2021 | Krivopisk | H04N 5/2258 |

FOREIGN PATENT DOCUMENTS

| | | |
|---|---|---|
| CN | 104224441 A | 12/2014 |
| CN | 204207828 U | 3/2015 |
| DE | 10 2006 019511 A1 | 10/2007 |
| EP | 2477392 A1 | 7/2012 |
| JP | 2005-074034 A | 3/2005 |
| JP | 2012-205849 A | 10/2012 |
| RU | 2177286 C2 | 2/2001 |
| WO | 200271991 A2 | 9/2002 |
| WO | WO2011/033513 A1 | 3/2011 |
| WO | 2011/030608 A1 | 2/2013 |
| WO | 2014110218 A1 | 7/2014 |
| WO | 2017100651 A1 | 6/2017 |

\* cited by examiner

CAMERA HEAD

FIELD OF THE INVENTION

The invention is from the field of video cameras. Specifically the invention relates to small diameter camera heads for use in such applications as medical endoscopes and laparoscopes and industrial borescopes.

BACKGROUND OF THE INVENTION

Ever since their first use it has been the goal of designers of medical endoscopes and laparoscopes and industrial borescopes to reduce the diameter of the instruments in order to allow access through smaller and smaller diameter orifices.

Methods of accomplishing reductions in the diameter are discussed for example in WO2011/033513 in which the Applicant of the present invention describes camera heads having an outer diameter of 1.4 mm or less.

Two of the obstacles to even further reduction in diameter are the flexible PCB substrates on which the sensor and other components of the camera head are generally mounted and the internal wiring that electrically connects the various electronic components. A third obstacle connected with small diameter camera heads such as those described in WO2011/033513 is the difficulty of assembly, in particular connecting the internal wiring, which is not suitable to mass production manufacturing.

A fourth obstacle is related to the need of integrated illumination in the aforementioned devices and the difficulty of transferring adequate amounts of current while maintaining the minimal dimensions of the camera-illumination assembly.

It is therefore a purpose of the present invention to provide a camera head which addresses the above mentioned obstacles.

Further purposes and advantages of this invention will appear as the description proceeds.

SUMMARY OF THE INVENTION

Disclosed herein is a video camera head that comprises a solid state sensor chip and optical and electrical components that are mounted on at least two rigid printed circuit boards (PCBs) arranged in parallel planes. The at least two PCBs are mechanically supported one above the other by at least two external pins that are attached to the perimeters of the PCBs. The external pins fit into grooves cut into the edges of the PCBs such that, in some embodiments, the external pins do not protrude outside of the circumferences of the PCBs.

In embodiments of the video camera head each of the external pins is made from one of: a rigid or a flexible or a semi-flexible material or a spring.

In embodiments of the video camera head comprise at least one of an objective optical system, illumination means, a housing of the objective optical system, and a camera head housing that surrounds all internal components of the camera head.

In the embodiments of the video camera head wherein all the external pins are made of an electrically insulating material, internal pins made of an electricity conducting material conduct electrical power through vias in the PCBs from the bottom PCB to electronic components or illumination means mounted on the other PCBs of the at least two PCBs and signals from a solid state sensor chip mounted on one of the other PCBs of the at least two PCBs to the bottom PCB. Some of these embodiments are comprised of three PCBs, wherein electronic components for receiving signals from a solid state sensor and outputting a video signal are mounted on the bottom PCB, a solid state sensor chip is mounted on the middle PCB, an objective optical system and illumination means are mounted on the top PCB.

In embodiments of the video camera head the external pins are made of an electrically conducting material. Electrical power is conducted from the bottom PCB to electronic components or illumination means mounted on the other PCBs of the at least two PCBs and signals from a solid state sensor chip mounted on one of the other PCBs of the at least two PCBs to the bottom PCB by both the external pins and internal pins that conduct the electric power and signals through vias in at least one of the PCBs. Some of these embodiments are comprised of three PCBs, wherein electronic components for receiving signals from a solid state sensor and outputting a video signal are mounted on the bottom PCB, a solid state sensor chip is mounted on the middle PCB, an objective optical system and illumination means are mounted on the top PCB. The external pins are made of electricity conducting material conduct electrical power from the bottom PCB to the top PCB and internal pins made of electricity conducting material conduct electrical power through vias in the PCBs from the bottom PCB to the middle PCB, and conduct signals from the sensor chip on the middle PCB to the bottom PCB.

In embodiments of the video camera head the external pins are made of an electrically conducting material and electrical power is conducted from the bottom PCB to electronic components or illumination means mounted on the other PCBs of the at least two PCBs and signals from a solid state sensor chip mounted on one of the other PCBs of the at least two PCBs to the bottom PCB by the external pins. Some of these embodiments are comprised of three PCBs, wherein electronic components for receiving signals from a solid state sensor and outputting a video signal are mounted on the bottom PCB, a solid state sensor chip is mounted on the middle PCB, an objective optical system and illumination means are mounted on the top PCB.

In embodiments of the video camera head the illumination means comprise at least one LED. In some of these embodiments the illumination means comprise an array of LEDs.

Embodiments of the video camera head are comprised of two PCBs, wherein electronic components for receiving signals from a solid state sensor and outputting a video signal are mounted on the bottom PCB, a solid state sensor chip is mounted on the top side of the bottom PCB, an objective optical system and illumination means are mounted on the top PCB. Internal pins made of electricity conducting material and/or external pins made of electrically conducting material conduct electrical power from the bottom PCB to the top PCB, electrical power from the bottom side to the top side of the bottom PCB, and conduct signals from the sensor chip on the top side to the bottom side of the bottom PCB. The internal pins conduct electric power and signals through vias in at least one PCB.

Embodiments of the video camera head are comprised of four PCBs, wherein electronic components for receiving signals from a solid state sensor and outputting a video signal are mounted on the bottom and second PCBs, a solid state sensor chip is mounted on the third PCB, an objective optical system and illumination means are mounted on the top PCB. Internal pins made of electricity conducting material and/or external pins made of electrically conducing material conduct electrical power from the first PCB to the second, third, and fourth PCBs and conduct signals from the sensor chip on the third PCB to the first PCB. The internal pins conduct electric power and signals through vias in the PCBs.

In embodiments of the video camera head at least some of the external pins are tubes of electrically insulating material through which optical fibers pass or tubular light guides and the illumination means are output couplers of the optical fibers or the light guides. The light source for the illumination means can be any conventional light source used with endoscopic systems; for example, at least one LED that is mounted on one of the PCBs in the camera head or proximally from it.

In embodiments of the video camera head some or all of the components of the objective optical system are mounted on the housing of the camera head.

In embodiments of the video camera head the PCBs are of any shape, symmetric or non-symmetric.

In embodiments of the video camera head of the invention some or all of the PCBs in a camera head can be different from the shapes and dimensions of other PCBs in the camera head.

In embodiments of the video camera head of the invention some or all of the components of the objective optical system can be mounted on a housing of the camera head.

All the above and other characteristics and advantages of the invention will be further understood through the following illustrative and non-limitative description of embodiments thereof, with reference to the appended drawing.

BRIEF DESCRIPTION OF THE DRAWING

FIGS. 4a to 8 schematically illustrate a third embodiment of the camera head of the invention.

DETAILED DESCRIPTION OF EMBODIMENTS OF THE INVENTION

Figure 1:
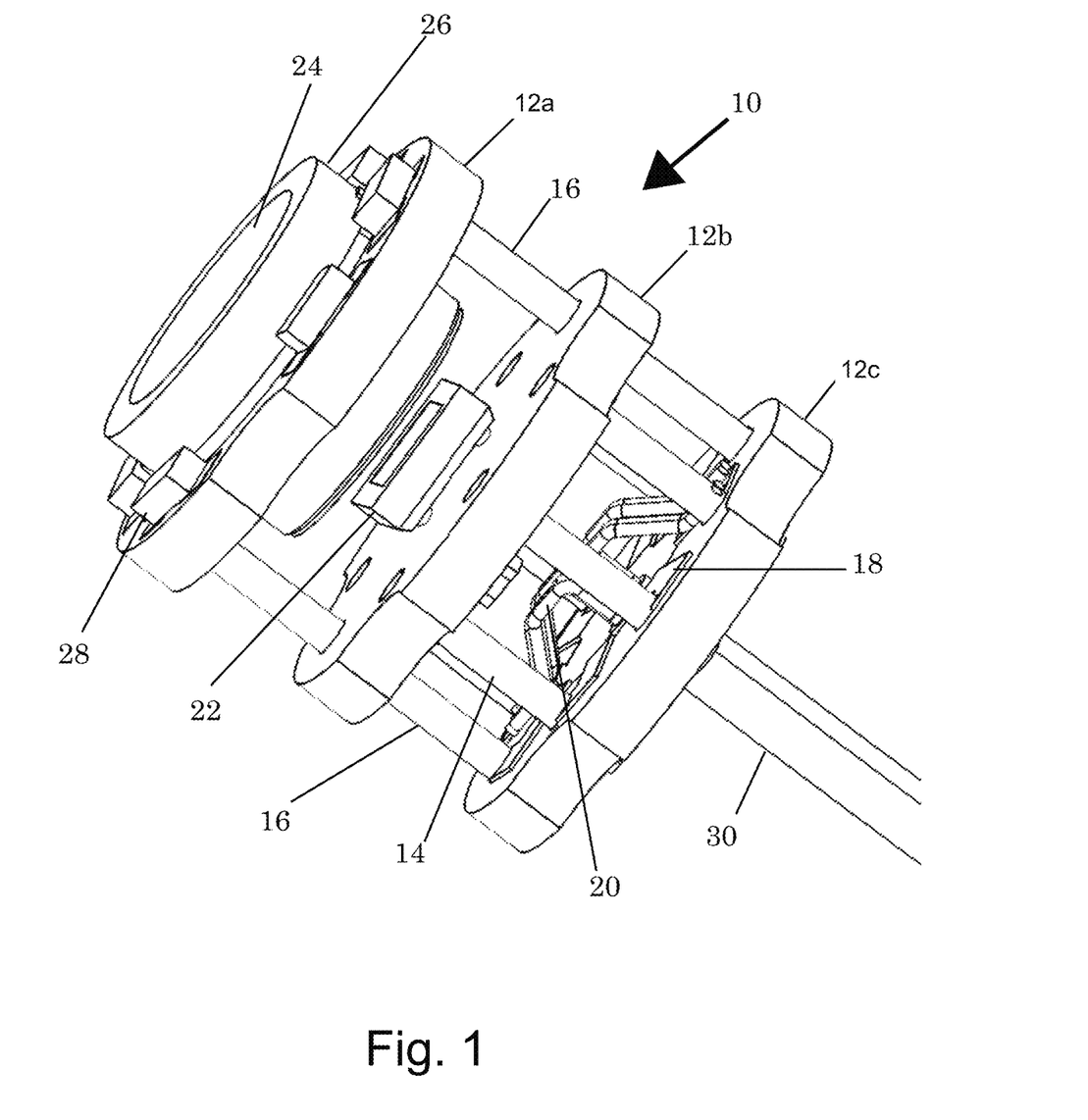
FIG. 1 schematically shows the structure of one embodiment of the camera head of the invention.

FIG. 1 schematically shows the structure of an embodiment of the camera head (10) of the invention. This embodiment of the camera head of the present invention comprises three rigid PCBs (12a, 12b, and 12c). The three PCBs are arranged in three parallel planes one above the other. (Note that for convenience the camera head is described as if it were oriented with its central axis vertical. This defines the relative directions such as top and bottom used herein.)

Figure 2:
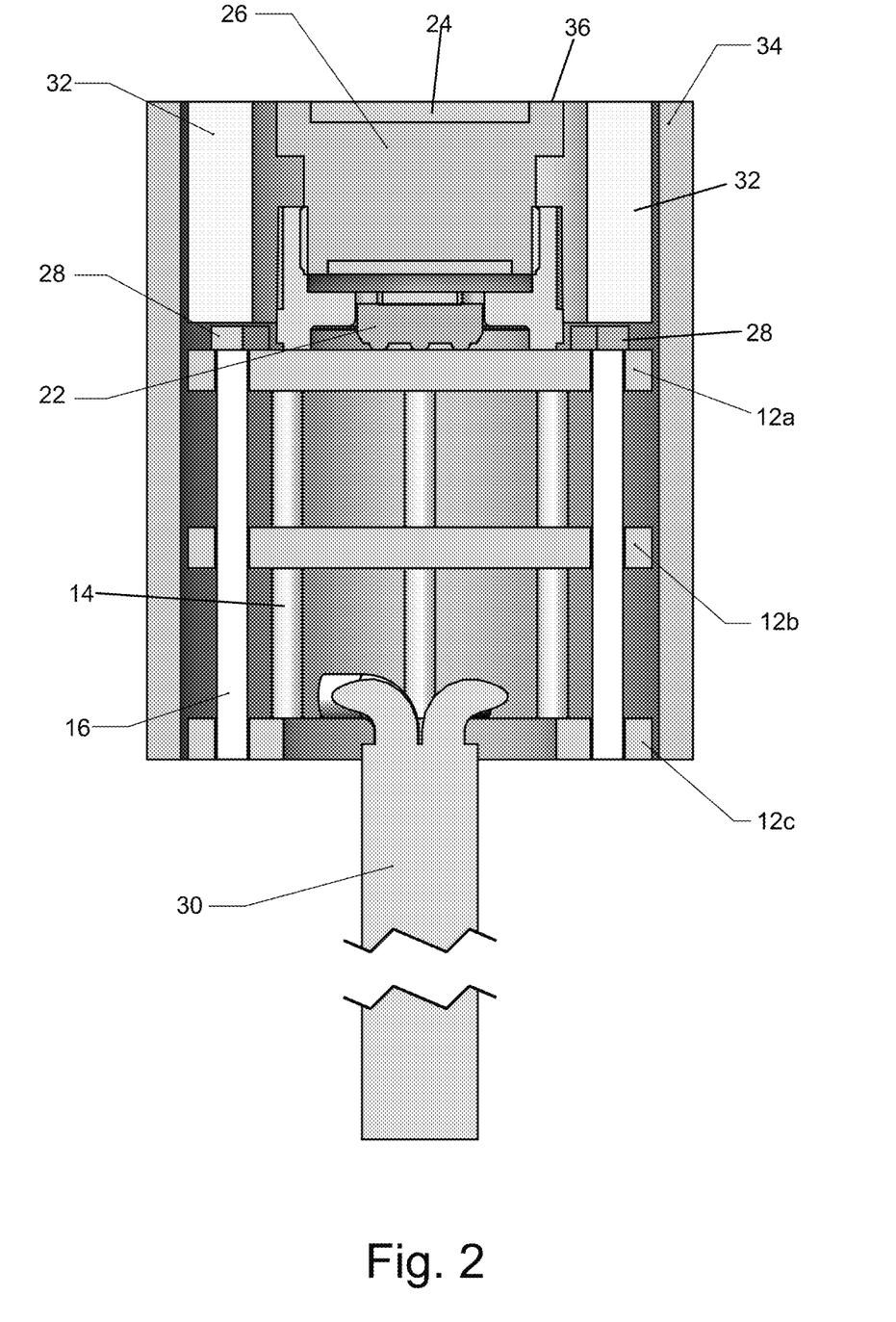
FIG. 2 and FIG. 3 schematically show a second embodiment of the camera head of the invention.
Figure 3:
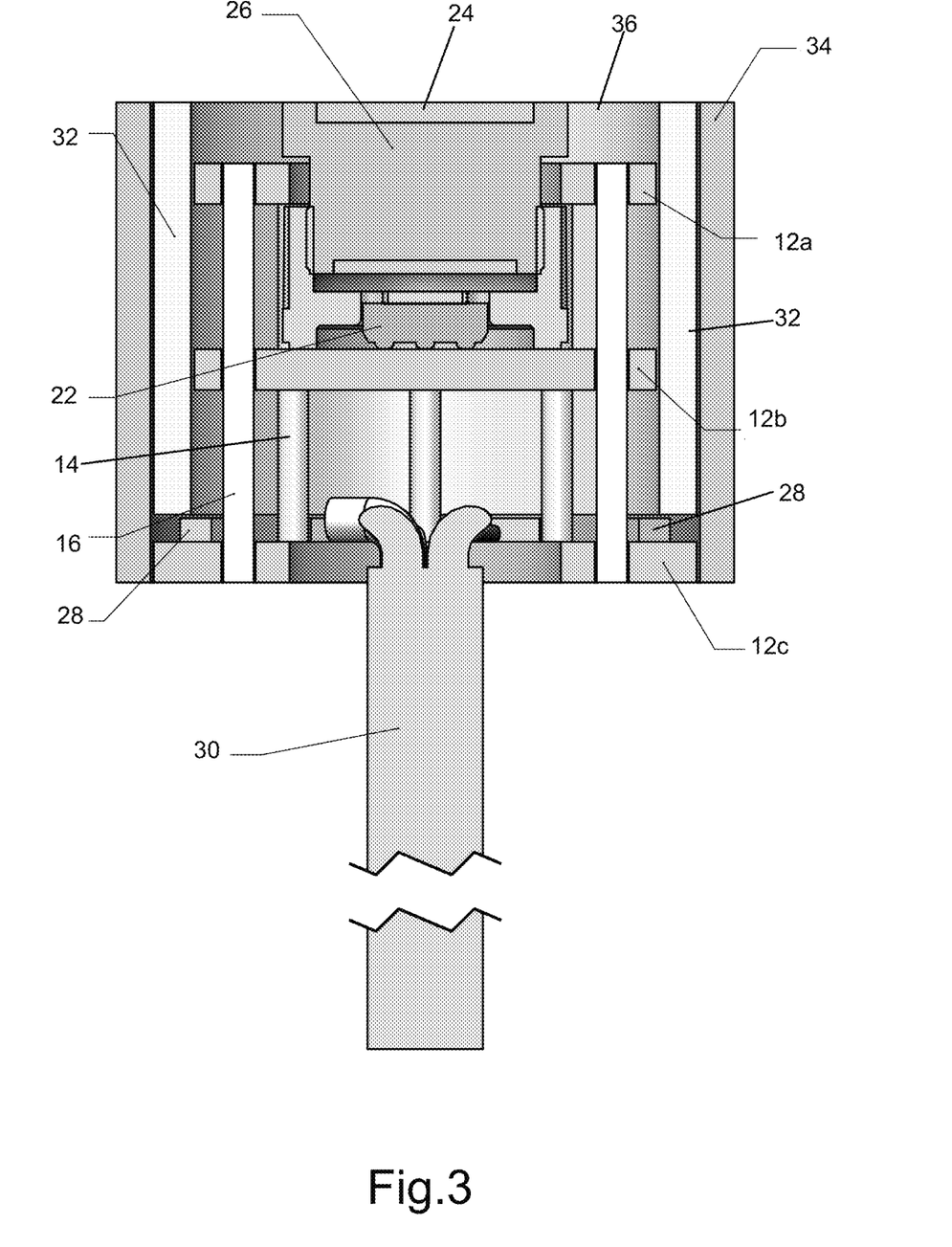

The middle PCB (12b) is mechanically supported above the lower PCB (12c) by six short pins (14) and the upper PCB (12a) is mechanically supported above the lower PCB (12c) by two longer pins (16) that pass through vias in PCB (12b). It is noted that embodiments of the camera head (10) may comprise more or less than 6 pins (14) and more than two pins (16). As is shown in FIGS. 1-3, all pins are located within the surface area of each of the PCBs and pass through vias in a PCB to reach the PCB above it.

Metallization (18) is created on the surface of the lower PCB (12c) and electronic components (20) for receiving signals from a solid state image sensor, e.g. CMOS, and outputting a video signal are electrically connected to this metallization. A camera cable (30) that conducts power to the camera head and video signals from it to a remote signal processor is connected by means of through vias to the metallization pattern on the top side of PCB (12c).

Middle PCB (12b) supports the solid state sensor chip (22).

The upper PCB (12a) supports the objective optical system (24) inside its housing (26) and illumination means, e.g. at least one LED or a ring array of LEDs (28) surrounding housing (26).

Pins (14) and (16) are made of electricity conducting material. Therefore they serve the dual purpose of mechanically supporting the upper two PCBs and also of conducting power to and signals from the sensor chip (22) and power to LEDs 28.

The internal structure of camera head (10) thus addresses all four of the obstacles discussed in the background section of this application. Firstly use of rigid PCBs instead of flexible PCBs eliminates the bending radius of the flexible PCB that usually increases the diameter of the camera head. Secondly the use of the electrically connecting pins allows for transferring adequate amounts of current for the illumination sources. Thirdly and fourthly the use of the electrically connecting pins eliminates most of the difficulty of making the internal wiring connections and therefore greatly simplifies the assembly process, thereby making camera head (10) into a device that is very suitable for mass production manufacturing.

It is noted that an embodiment of the camera head of the invention can comprise two PCBs in which case the electronic components are located on the bottom surface of the lower PCB and the sensor chip on the top surface of the bottom PCB and the objective lens system and illumination source on the upper PCB. Other embodiments can comprise more than three PCBs, for example four in which the lower two PCBs support electronic components, the third PCB supports the sensor chip and the top PCB supports the objective optical system and illumination means. In all embodiments electricity conducting pins serve the dual purposes of separating and mechanically supporting the PCBs and of conducting electric power and video signals between them.

In other embodiments of the invention the illumination means supported on the uppermost PCB are output couplers of optical fibers or light guides. In these embodiments the light source can be any conventional light source used with endoscopic systems, e.g. LEDs that can be mounted on one of the lower PCBs in the camera head or proximally from it. In some embodiments the electrically conducting pins may be combined with hollow light guides.

In one embodiment, shown schematically in FIG. 2, the camera head comprises three PCBs that are mechanically supported one above the other by electricity conducting pins 14,16. The two lower PCBs 12b,12c support electronic components (not shown in the figure) for receiving signals from a solid state image sensor 22 and outputting a video signal. The uppermost PCB 12a supports the solid state sensor 22 and one or more LEDs 28, e.g. a circular array, which surround the sensor. In this embodiment an objective lens system 24 enclosed in its housing 26 is held in place above the sensor 22 by a support structure, e.g. a hollow tube attached at its bottom end to the PCB 12a or by a structure attached to a camera housing 34 that surrounds the internal components of the camera head. The camera head also comprises vertical tubular light guides 32, which transfer light from the LEDs 28 to the height of the objective lens 24 on the distal end 36 of the camera housing 34 facing the object to be imaged. The light guides 32 are supported above the LEDs 28, for example by being attached at their bottom ends to the PCB 12a or by supports attached to the interior of the camera housing 34.

The electronic components located on PCBs 12a and 12b can be redistributed onto one PCB only and/or some can be located on PCB 12a thereby allowing this embodiment of the camera head to comprise only two PCBs. In all embodiments camera cable 30 is connected to electronic components on the bottom PCB.

A variation of the embodiment shown in FIG. 2 is shown schematically in FIG. 3. In the camera head shown in FIG. 3, electronic components (not shown) are located on PCBs 12a and 12c (and in some versions also on 12b), the LEDs 28 are on PCB 12c and light guides 32 transfer light from the LEDs 28 to the height of the objective lens 24 the distal end 36 of the camera housing 34 facing the object to be imaged.

In other embodiments the light source can be located remotely from the camera head and the light transferred directly from the light source to an output coupler on the distal end 36 of the camera housing 34 or alternately to one of the PCBs where it is coupled into a hollow light guide as shown in FIGS. 2 and 3.

Another configuration of a camera head is schematically illustrated in FIG. 4a to FIG. 8. In this configuration at least two rigid PCBs on which optical and electronic components are located at supported one above the other by external pins attached to the perimeters of the PCBs. The external pins can have various forms, e.g., solid wires or hollow rods made of electrically conductive or electrically isolative material the external pins can be rigid or they can be flexible, semi flexible, or a spring, in order to give flexibility to the entire structure of the camera head. The external pins of this embodiment are so named to distinguish them from the internal pins (14) and (16) of the first and second embodiments described herein above. Because the external pins provide the structure for supporting the PCBs, in this structure the function of the internal pins is to transfer electric power and video signals so none of them have to be rigid but some or all of the internal pins can be flexible, semi flexible, or springs.

In different embodiments of this configuration that are described herein below, some or all of the internal pins can be deleted and power and signals conducted between the PCBs via electrically conducting external pins. This simplifies the manufacturing and assembly times of the camera heads.

Figure 4A:
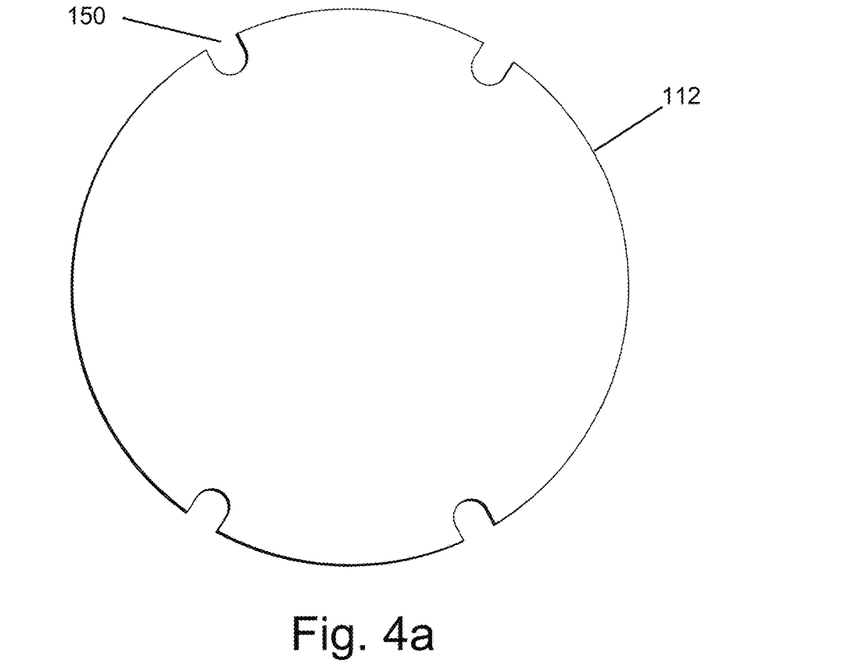
Figure 4B:
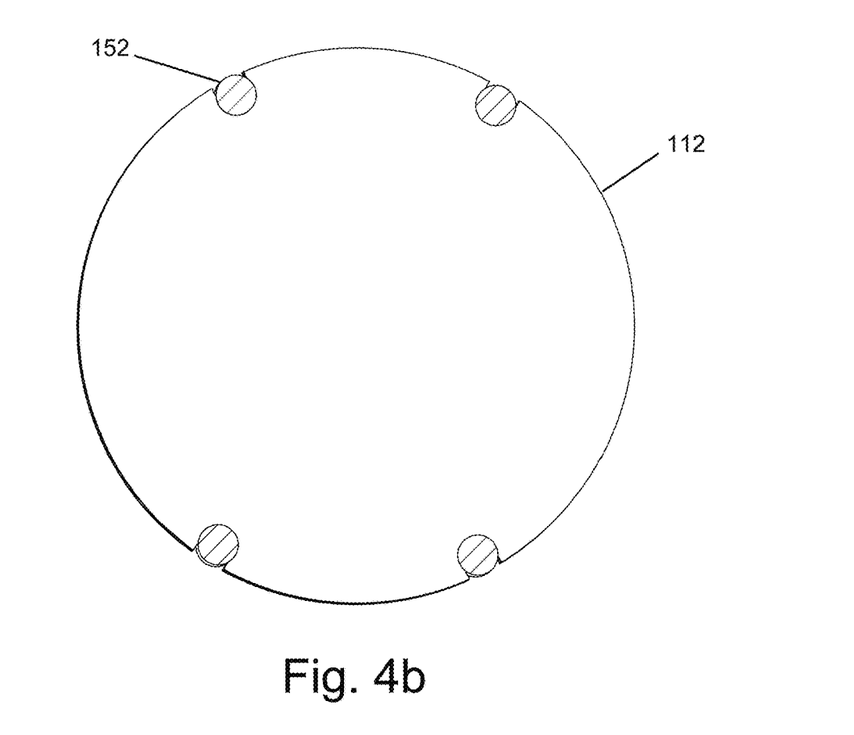

FIG. 4a schematically shows a top view of a PCB (112) of the type used in the camera heads of the present structure. Around the circumference of the PCB U-shaped grooves (150) are cut into the edges of the PCB. FIG. 4b schematically shows PCB (112) with external pins (152) fitted into grooves (150). External pins (152) can be attached to PCB (112) by several means, e.g. press fitting into grooves (150) and held by friction or by use of epoxy or another adhesive. Since, as described below, all or some of these external pins are used not only for support but also as electrical conductors they will be soldered to the PCB and in such a case adhesive or other means to attached them to the PCB are not required.

In FIGS. 4a and 4b there are shown four grooves (150) and corresponding external pins (152) but it is to be understood that in principle two external pins (152) could be enough to perform the desired support function. However, three external pins (152) would provide a more stable structure, and in embodiments, such as some of those described herein below, more than four external pins can be required. Also, although PCBs (112) and external pins (152) having circular cross-sections are described and illustrated herein; other cross-sectional shapes, symmetric or non-symmetric, can be used. If the cross-sectional shapes of the external pins (152) are not circular, then the shapes of grooves (150) have to be suitable to accommodate the external pins (152).

As shown in FIG. 4b, the depths of grooves (150) are no less than the diameter of external pins (152) so that the external pins (152) do not protrude outside of the circumference of the PCB (112). Therefore, in this case the maximum cross-sectional diameter of the camera head is determined by the diameter of the PCB (112). In other camera heads, the depth of grooves 150 could be such that the external pins (152) could protrude outside of the circumference of the PCB (112) as long as the overall diameter of the camera head does not exceed the design requirements.

Figure 5:
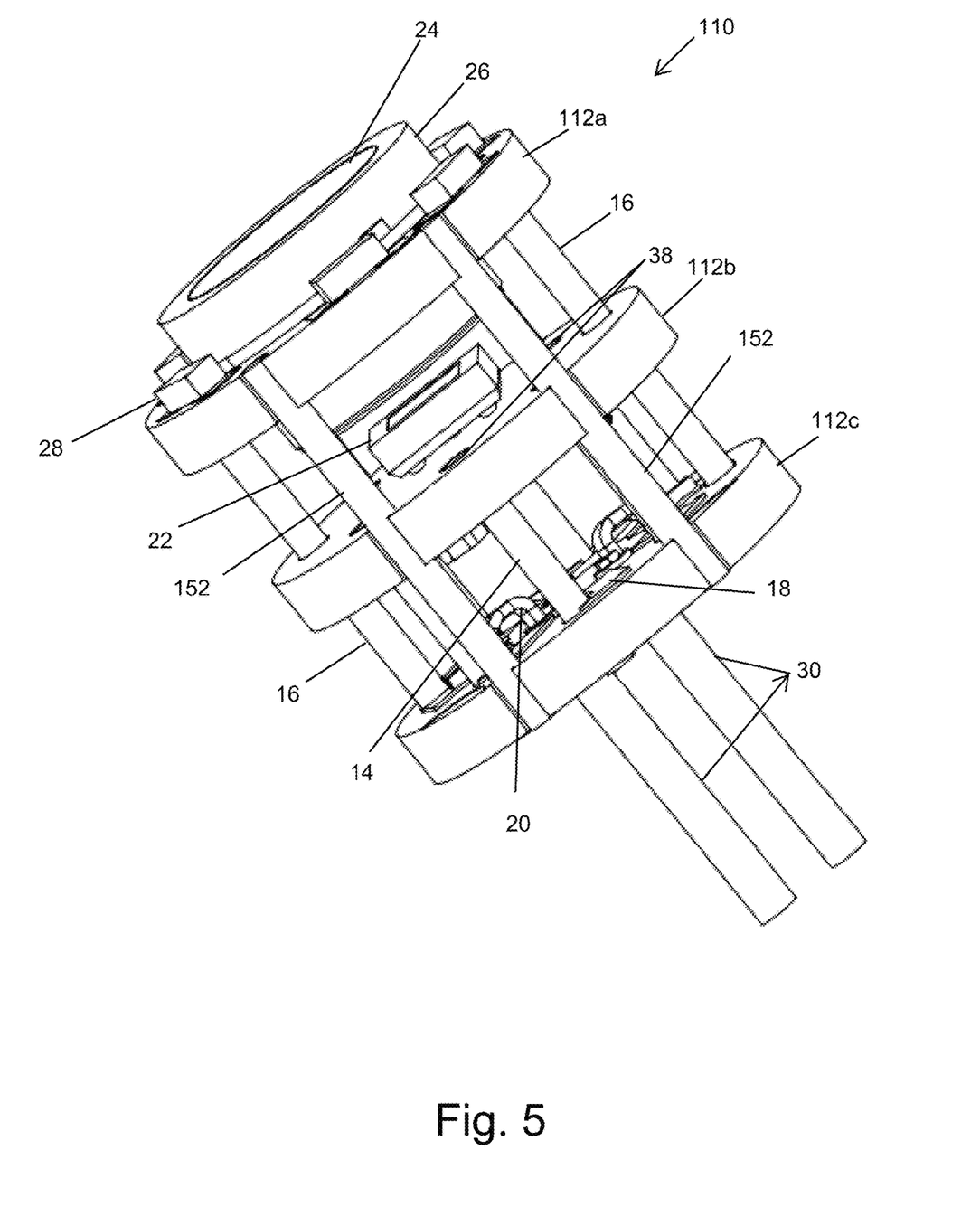

FIG. 5 shows a camera head (110) that is similar to the camera head (10) of the first embodiment shown in FIG. 1. FIG. 5 differs from FIG. 1 by the addition of external pins (152) that support PCBs (112b) and (112a) above PCB (112c). This embodiment and all embodiments of the camera head described below can comprise a camera housing (34) that surrounds the internal components of the camera head (see FIGS. 2 and 3).

In the camera head (110) of FIG. 5 metallization (18), i.e. electricity conductive paths, is created on the surface of the lower PCB (112c) and electronic components (20) for receiving signals from a solid state image sensor, e.g. a CMOS sensor, and outputting a video signal are electrically connected to this metallization. A camera cable (30) that conducts power to the camera head and video signals from it to a remote signal processor is connected by means of through vias to the metallization pattern on the top side of PCB (112c). In other embodiments the circuits on the PCBs can be designed so that the camera cable or a few of the wires in the cable are connected to components on a PCB (112A or 112B). Middle PCB (112b) supports the solid state sensor chip (22) and the upper PCB (112a) supports the objective optical system (24) inside its housing (26) and illumination means, e.g. at least one LED (28) or a ring array of LEDs surrounding housing (26). In the embodiment of FIG. 5 internal short pins (14) and long pins (16) that are made of electricity conducting material pass through vias (38) in PCBs (112b) and (112a) to conduct power to and signals from the sensor chip (22) and power to LEDs (28).

In the camera head of FIG. 5 the external pins (152) can either be made of an electrically conducting material, e.g. a metallic wire, or an insulator, e.g. rigid plastic or ceramic. External pins (152) can be rigid, flexible, or springs.

Figure 6:
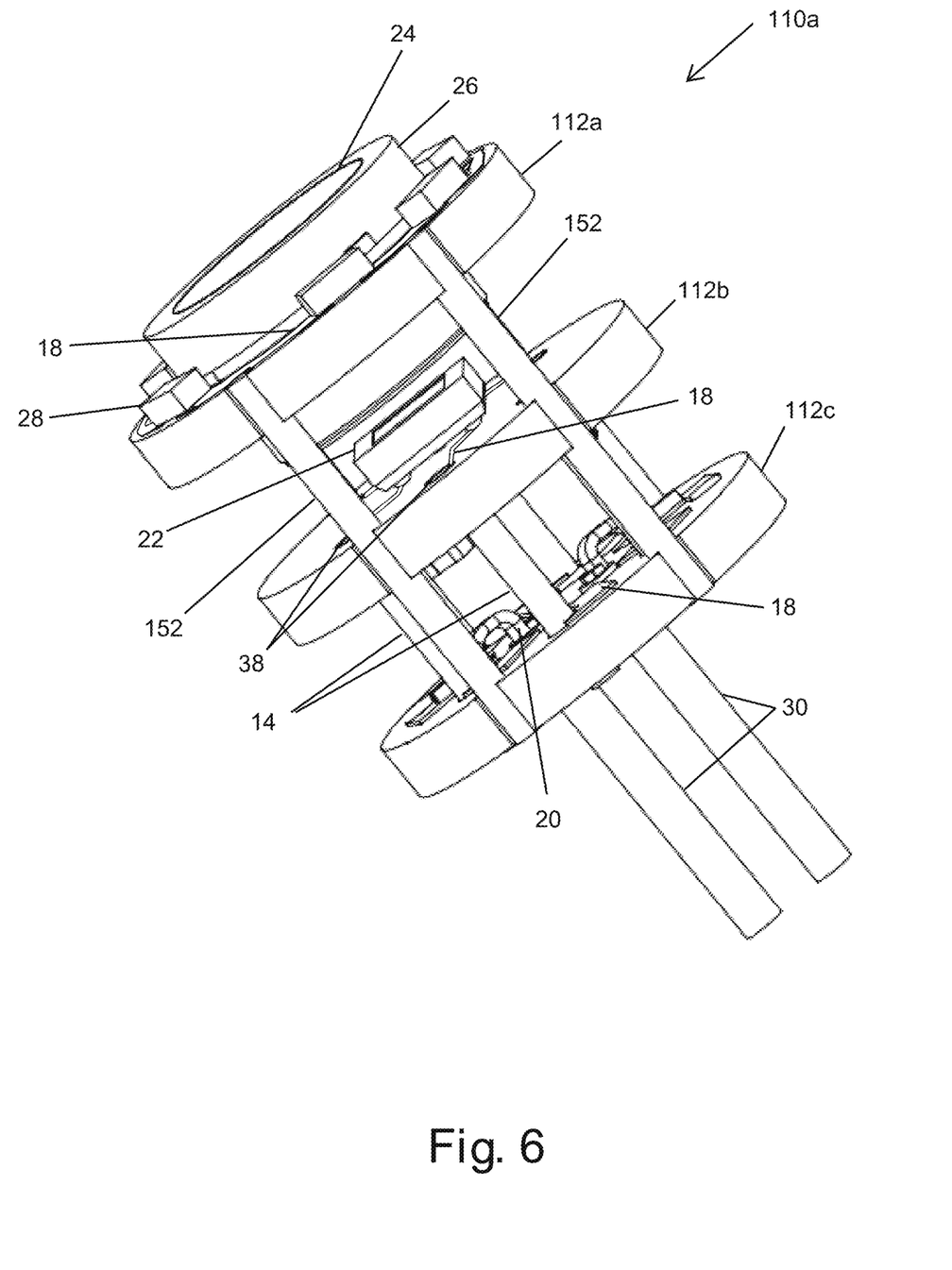

FIG. 6 schematically shows a camera head (110a), which is a variation of the camera head (100) of FIG. 5 in which the internal long pins (16) are removed. In the embodiment shown in FIG. 6, the external pins (152) are made of an electrically conducting material, e.g. metallic wires, and metallization (18) is added to PCB (112a) in order to electrically connect the LEDs (28) to the tops of external pins (152) which are connected to the PCB (112a) and metallization (18) by any known means such as solder or electricity conducting epoxy. In this embodiment power is transmitted from the electrical components (20) via metallization (18) and a solder or conducting epoxy joint on PCB (112c) to the bottom of the external pins (152) and from there to the LEDs (18) on PCB (112a).

In this embodiment internal short pins (14) continue to conduct power to the sensor (22) on PCB (112b) from the electrical components (20) on PCB (112c) and video signals from sensor (22) back to PCB (112c) via metallization (18) on both PCBs and vias (38) on PCB (112b).

Figure 7:
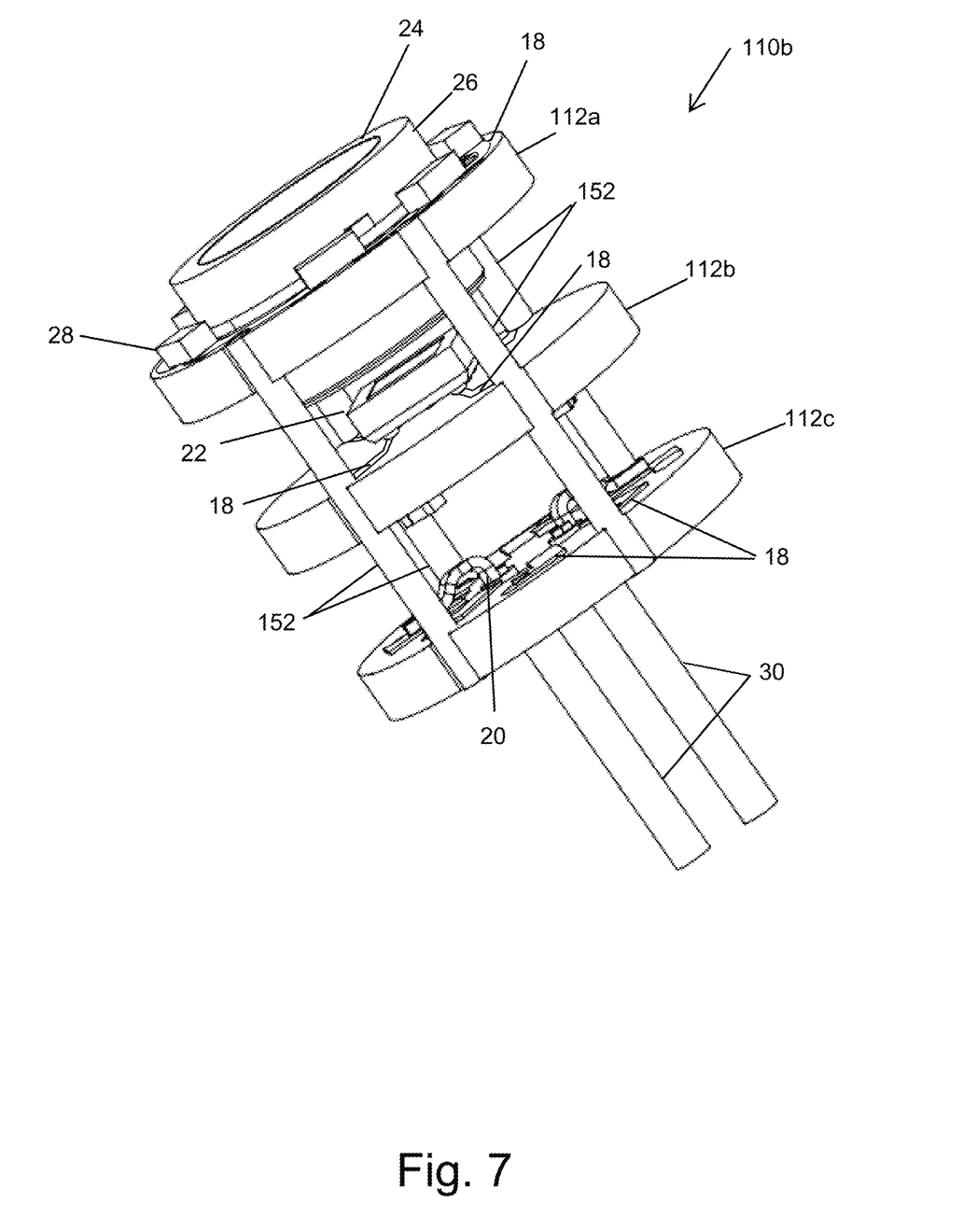

FIG. 7 schematically shows a camera head (110b), which is an embodiment of the camera head (100) of FIG. 5 in which, in addition to removal of the internal long pins (16), also the internal short pins (14) are removed. In camera head (100*b*) PCB (112*b*) no longer has any vias (38) and the metallization (14) electrically connects the contact balls on the bottom of the sensor (22) to several of the electricity conducting external pins (152) in order to conduct power to and signals from sensor (22).

It is noted that in addition to being comprised of a single piece of metal wire, electricity conducting external pins (152) can be formed in other ways, for example from a metal wire coated with an electrical insulating material or an uninsulated metal wire or one or a pair of wires embedded in channels in an insulating material. The only criteria being that the external pins (152) are sufficiently strong to support the PCBs above each other and that the conducting wires are capable of carrying the current needed to supply the power needed to activate the LEDs (28) and/or sensor (22).

Figure 8:
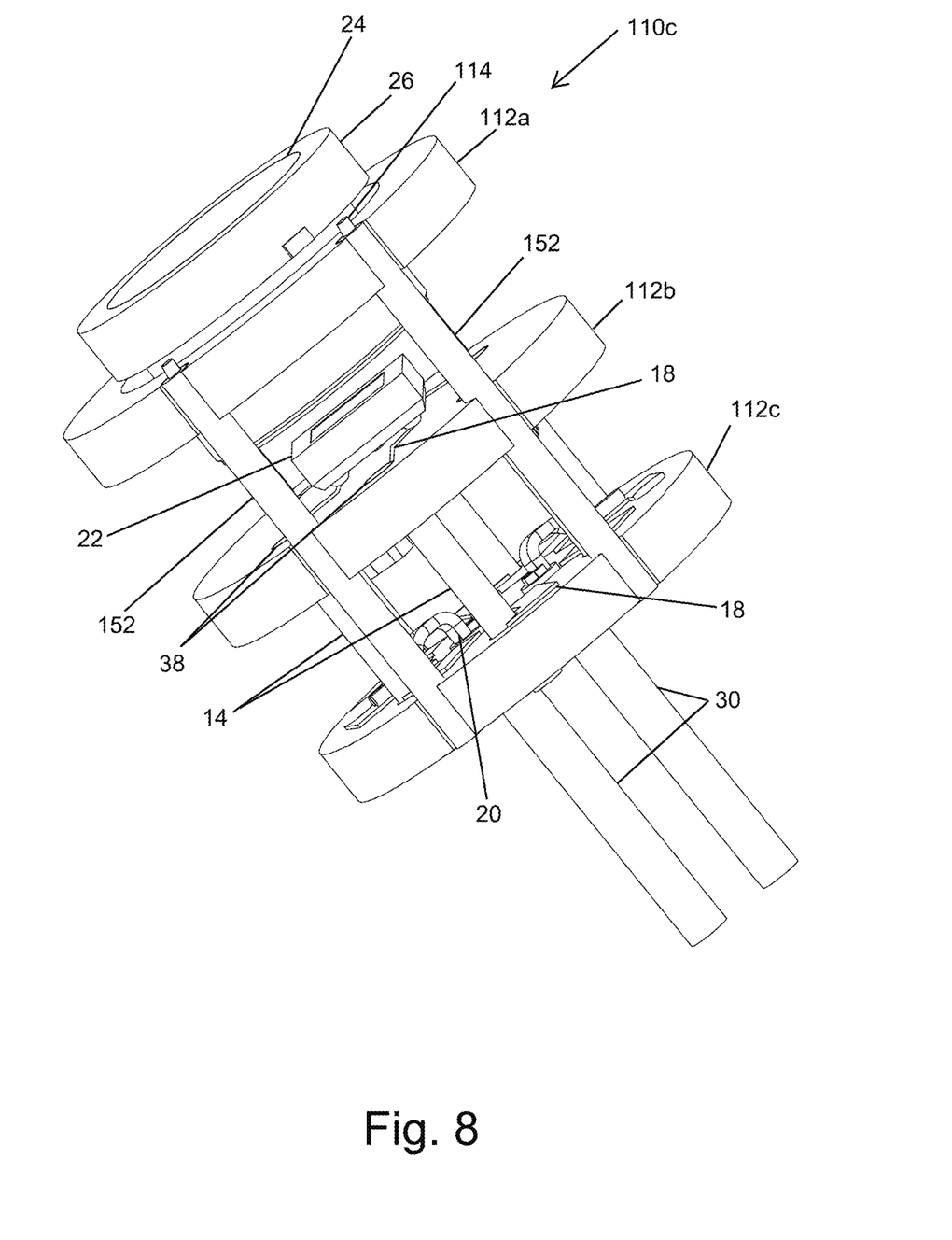

FIG. 8 schematically shows a camera head (110*c*), which is an embodiment of the camera head (100) of FIG. 5 in which, in addition to removal of the internal long pins (16), also the LEDs (28) and metallization (18) on PCB (112*a*) are removed. In camera head (110*c*) the external pins (152) are tubes of electrically insulating material through which optical fibers pass or tubular light guides either of which guide light from a light source, e.g. one or more LEDs, which are some of the electronic components (18) on PCB (112*c*), or from a remote source via camera cable (30) and electronic components (18). At the top of the light guides/external pins (152) on PCB (112*a*) are schematically shown optical output coupling elements (114). In this figure only two light guides are seen, but, depending on the amount of illumination needed for the sensors to capture images of a desired quality, several additional light guides/external pins (152), e.g. 4-6 or more can be present.

Camera heads having the structure comprising external pins (152) can be manufactured in many different variations and the embodiments described herein above represent only a small selection that is intended to disclose the principal features of the structure. An example of an embodiment based on the above description is a camera head that comprises two PCBs in which case the electronic components are located on the bottom surface of the lower PCB and the sensor chip on the top surface of the bottom PCB and the objective lens system and illumination source on the upper PCB. Other embodiments can comprise more than three PCBs, for example four in which the lower two PCBs support electronic components, the third PCB supports the sensor chip and the top PCB supports the objective optical system and illumination means. In all embodiments the PCBs are mechanically supported above each other by external pins (152) and electric power and video signals are transported between components on the PCBs by electricity conducting external pins (152), electricity conducting internal pins (14,16), or combinations of external pins (152) and internal pins (14,16).

Although embodiments of the invention have been described by way of illustration, it will be understood that the invention may be carried out with many variations, modifications, and adaptations, without exceeding the scope of the claims.

The invention claimed is:

1. A video camera head comprising a solid state sensor chip and optical and electrical components mounted on at least two rigid printed circuit boards (PCBs) arranged in parallel planes, wherein the at least two PCBs are mechanically supported one above the other by at least two external pins attached to the perimeters of the PCBs, wherein the external pins fit into grooves cut into the edges of the PCBs; and wherein one or more internal pins made of an electricity conducting material are configured to conduct electrical power through vias in the PCBs from a bottom PCB to electronic components or illumination means mounted on other PCBs of the at least two PCBs and signals from a solid state sensor chip mounted on one of the other PCBs of the at least two PCBs to the bottom PCB.

2. The video camera head of claim 1 wherein each of the external pins is made from one of: a rigid or a flexible or semi flexible material or a spring.

3. The video camera head of claim 1 wherein each of the external pins is made from one of: an electrically conducting material or an electrically insulating material.

4. The video camera head of claim 1 comprising at least one of an objective optical system, illumination means, a housing of the objective optical system, and a camera head housing that surrounds all internal components of the camera head.

5. The video camera head of claim 4 wherein all the external pins are made of an electrically insulating material.

6. The video camera head of claim 5 comprised of three PCBs, wherein electronic components for receiving signals from a solid state sensor and outputting a video signal are mounted on the bottom PCB, a solid state sensor chip is mounted on the middle PCB, an objective optical system and illumination means are mounted on the top PCB.

7. The video camera head of claim 4 wherein the external pins are made of an electrically conducting material and electrical power is conducted from the bottom PCB to electronic components or illumination means mounted on the other PCBs of the at least two PCBs and signals from a solid state sensor chip mounted on one of the other PCBs of the at least two PCBs to the bottom PCB by both the external pins and the one or more internal pins.

8. The video camera head of claim 7 comprised of three PCBs, wherein electronic components for receiving signals from a solid state sensor and outputting a video signal are mounted on the bottom PCB, a solid state sensor chip is mounted on the middle PCB, an objective optical system and illumination means are mounted on the top PCB, the external pins made of electricity conducting material conduct electrical power from the bottom PCB to the top PCB and internal pins made of electricity conducting material conduct electrical power through vias in the PCBs from the bottom PCB to the middle PCB, and conduct signals from the sensor chip on the middle PCB to the bottom PCB.

9. The video camera head of claim 4 wherein the external pins are made of an electrically conducting material and electrical power is conducted from the bottom PCB to electronic components or illumination means mounted on the other PCBs of the at least two PCBs and signals from a solid state sensor chip mounted on one of the other PCBs of the at least two PCBs to the bottom PCB by the external pins.

10. The video camera head of claim 9 comprised of three PCBs, wherein electronic components for receiving signals from a solid state sensor and outputting a video signal are mounted on the bottom PCB, a solid state sensor chip is mounted on the middle PCB, an objective optical system and illumination means are mounted on the top PCB.

11. The video camera head of claim 4 wherein the illumination means comprise at least one LED.

12. The video camera head of claim 11 wherein the illumination means comprise an array of LEDs.

13. The video camera head of claim 4 comprised of two PCBs, wherein electronic components for receiving signals from a solid state sensor and outputting a video signal are mounted on the bottom PCB, a solid state sensor chip is mounted on the top side of the bottom PCB, an objective optical system and illumination means are mounted on the top PCB; wherein the one or more internal pins and/or external pins made of electrically conducing material conduct electrical power from the bottom PCB to top PCB, electrical power from the bottom side to the top side of the bottom PCB, and conduct signals from the sensor chip on the top side to the bottom side of the bottom PCB; wherein the internal pins conduct electric power and signals through vias in the PCBs.

14. The video camera head of claim 4 comprised of four PCBs, wherein electronic components for receiving signals from a solid state sensor and outputting a video signal are mounted on the bottom and second PCBs, a solid state sensor chip is mounted on the third PCB, an objective optical system and illumination means are mounted on the top PCB; wherein the one or more internal pins and/or external pins made of electrically conducing material conduct electrical power from the first PCB to the second, third, and fourth PCBs and conduct signals from the sensor chip on the third PCB to the first PCB; wherein the internal pins conduct electric power and signals through vias in the PCBs.

15. The video camera head of claim 4 wherein at least some of the external pins are tubes of electrically insulating material through which optical fibers pass or tubular light guides and the illumination means are output couplers of the optical fibers or the light guides.

16. The video camera of claim 15 wherein a light source for the illumination means is any conventional light source used with endoscopic systems.

17. The video camera of claim 16 wherein the light source is at least one LED that is mounted on one of the PCBs in the camera head or proximally from it.

18. The video camera head of claim 4, wherein some or all of the components of the objective optical system are mounted on the housing of the camera head.

19. The video camera of claim 1 wherein the PCBs are of any shape, symmetric or non-symmetric.

* * * * *